United States Patent [19]
Ill et al.

[11] Patent Number: 5,843,770
[45] Date of Patent: Dec. 1, 1998

[54] ANTISENSE CONSTRUCTS DIRECTED AGAINST VIRAL POST-TRANSCRIPTIONAL REGULATORY SEQUENCES

[75] Inventors: Charles R. Ill, Encinitas; Jose E. N. Gonzales, San Diego, both of Calif.

[73] Assignee: The Immune Response Corporation, Carlsbad, Calif.

[21] Appl. No.: 613,861

[22] Filed: Mar. 11, 1996

[51] Int. Cl.⁶ .......................... C12N 15/00; C07H 21/02; C07H 21/04; C12P 19/34
[52] U.S. Cl. .................. 435/320.1; 435/91.1; 536/24.1; 536/24.5
[58] Field of Search ............................. 435/91.31, 91.1, 435/320.1; 514/44; 536/23.1, 23.2, 24.1, 24.3, 24.5; 935/27

[56] References Cited

PUBLICATIONS

Oh et al "Application of Antisense Oligodeoxyribonuceotides in the control of Hepatits B Replication" Korean J. of Biochemistry vol. 26: 237–247, 1994.
Milligan et al., "Current Concepts in Antisense Drug Design", J. Medicinal Chemistry. vol. 36(14):1923–1937, 1993.
Westermann et al., "Inhibition of Expression of SV40 virus large T–antigen by antisense oligonucleotides", Biomed. Biochim. Acta. vol. 48:85–93, 1989.
Bennet, "Antisense Research", Science. vol. 271:434, 1996.
Weiss, "Upping the Antisense Ante", Science News. vol. 139:108–109, 1991.
Stein et al., "Antisense Oligonucleotides as Therapeutic Agents–Is the Bullet Really Magical?", Science. vol. 261:1004–1012, 1993.
Wagner, "Gene Inhibition Using Antisense Oligonucleotides", Nature. vol. 372:333–335, 1994.
Stull et al., "Antigene, Ribozyme and Aptamer Nucleic Acid Drugs: Progress and Prospects", Pharmaceutical Research. vol. 12(4):465–483, 1995.
Wu–Pong, "Oligonucleotides: Opportunities for Drug Therapy Research", Pharmaceutical Technology. vol. 18:102–114,1994.
Gura, "Antisense Has Growing Pains", Science vol. 270:575–577,1995.
Miller et al, "Gene Transfer and Antisense Nucleic Acid Techniques", Parisitology Today. vol. 10(3): 92–97, 1994.
Rojanasakul, "Antisense Oligonucleotide Therapeutics: Drug Delivery and Targeting", Advanced Drug Delivery Reviews. vol. 18:115–131,1996.

Fenster et al "Inhibition of Human Immunodeficency Virus Type–1 env Expression by C–5 Propyne Oligonucleotides Specific for Rev–Respose element stem loop V." Biochemistry vol. 33: 8391–8398, 1994.
Benitez, L.V. and J.E. Halver (1982), "Ascorbic acid sulfate sulfohydrolase ($C_2$ sulfatase): The modulator of cellular levels of L–ascorbic acid in rainbow trout", *Proc. Natl. Acad. Sci. USA* 79:5445–5449.
"Drug Facts and Comparisons", 1992 Edition, eds. Olin, B.R. et al., St. Louise, MO, pp. 2445–2460.
Huang, J. and T.J. Liang (1993), "A Novel Hepatits B Virus (HBV) Genetic Element with Rev Response Element–Like Properties That is Essential for Expression of HBV Gene Products", *Mol. and Cell. Biol.* 13:7476–7486.
Huang, Z–M. and T.S.B. Yen (1994), "Hepatitis B Virus RNA Element That Facilitates Accumulation of Surface Gene Transcripts in the Cytoplasm", *J. Virol.* 68:3193–3199.
Huang, Z–M. and T.S.B. Yen (1995), "Role of the Hepatitis B Virus Posttransitional Regulatory Element in Export of Intronless Transcripts", *Mol. and Cell. Biol.* 15:3864–3869.
Huang, Z–M. et al. (1996), "Cellular Proteins That Bind to the Hepatitis B Virus Posttransitional Regulatory Element", *Virology* 217:573–581.
Wu, C.H. et al. (1989), "Targeting Genes: Delivery and Persistent Expression of a Foreign Gene Driven by Mammalian Regulatory Elements in Vivo", *J. Biol. Chem.* 264:16985–16987.
Wu, G.Y. and C.H. Wu (1987), "Receptor–mediated in Vitro Gene Transformation by a Soluble DNA Carrier System", *J. Biol. Chem.* 262:4429–4432.
Wu, G.Y. and C.H. Wu (1988), "Receptor–mediated Gene Delivery and Expression in Vivo", *J. Biol. Chem.* 263:14621–14624.

*Primary Examiner*—George C. Elliot
*Assistant Examiner*—Sean McGarry
*Attorney, Agent, or Firm*—Lahive & Cockfield,LLP; Jane E. Remillard, Esq.

[57] ABSTRACT

Antisense constructs ditrected against viral cis-acting post-transcriptional regulatory sequences ("PREs") are disclosed. In one embodiment, the antisense construct is an expression plasmid encoding one or more antisense transcripts which hybridize under intracellular conditions to all or a portion of a viral PRE within a viral transcript, the PRE having the function of directing export of the viral transcript from the nucleus to the cytoplasm of a cell. The antisense constructs can be used to inhibit viral production, such as HBV production.

11 Claims, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 587 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:1:

```
CCTTTCTAAG  TAAACAGTAC  ATGAACCTTT  ACCCCGTTGC  TCGGCAACGG  CCTGGTCTGT      60
GCCAAGTGTT  TGCTGACGCA  ACCCCCACTG  GCTGGGGCTT  GGCCATAGGC  CATCAGCGCA     120
TGCGTGGAAC  CTTTGTGGCT  CCTCTGCCGA  TCCATACTGC  GGAACTCCTA  GCCGCTTGTT     180
TTGCTCGCAG  CCGGTCTGGA  GCAAAGCTCA  TCGGAACTGA  CAATTCTGTC  GTCCTCTCGC     240
GGAAATATAC  ATCGTTTCCA  TGGCTGCTAG  GCTGTACTGC  CAACTGGATC  CTTCGCGGGA     300
CGTCCTTTGT  TTACGTCCCG  TCGGCGCTGA  ATCCCGCGGA  CGACCCCTCT  CGGGGCCGCT     360
TGGGACTCTC  TCGTCCCCTT  CTCCGTCTGC  CGTTCCAGCC  GACCACGGGG  CGCACCTCTC     420
TTTACGCGGT  CTCCCCGTCT  GTGCCTTCTC  ATCTGCCGGT  CCGTGTGCAC  TTCGCTTCAC     480
CTCTGCACGT  TGCATGGAGA  CCACCGTGAA  CGCCCATCAG  ATCCTGCCCA  AGGTCTTACA     540
TAAGAGGACT  CTTGGACTCC  CAGCAATGTC  AACGACCGAC  CTTGAGG                    587
```

( 2 ) INFORMATION FOR SEQ ID NO:2:

( i ) SEQUENCE CHARACTERISTICS:
        ( A ) LENGTH: 4525 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:2:

```
CAGGTGGCAC  TTTTCGGGGA  AATGTGCGCG  GAACCCCTAT  TTGTTTATTT  TTCTAAATAC      60
ATTCAAATAT  GTATCCGCTC  ATGAGACAAT  AACCCTGATA  AATGCTTCAA  TAATATTGAA     120
AAAGGAAGAG  TATGAGTATT  CAACATTTCC  GTGTCGCCCT  TATTCCCTTT  TTTGCGGCAT     180
TTTGCCTTCC  TGTTTTTGCT  CACCCAGAAA  CGCTGGTGAA  AGTAAAAGAT  GCTGAAGATC     240
AGTTGGGTGC  ACGAGTGGGT  TACATCGAAC  TGGATCTCAA  CAGCGGTAAG  ATCCTTGAGA     300
GTTTTCGCCC  CGAAGAACGT  TTTCCAATGA  TGAGCACTTT  TAAAGTTCTG  CTATGTGGCG     360
CGGTATTATC  CCGTATTGAC  GCCGGGCAAG  AGCAACTCGG  TCGCCGCATA  CACTATTCTC     420
AGAATGACTT  GGTTGAGTAC  TCACCAGTCA  CAGAAAAGCA  TCTTACGGAT  GGCATGACAG     480
TAAGAGAATT  ATGCAGTGCT  GCCATAACCA  TGAGTGATAA  CACTGCGGCC  AACTTACTTC     540
TGACAACGAT  CGGAGGACCG  AAGGAGCTAA  CCGCTTTTTT  GCACAACATG  GGGGATCATG     600
```

| | | | | | |
|---|---|---|---|---|---|
| TAACTCGCCT | TGATCGTTGG | GAACCGGAGC | TGAATGAAGC | CATACCAAAC | GACGAGCGTG | 660 |
| ACACCACGAT | GCCTGTAGCA | ATGGCAACAA | CGTTGCGCAA | ACTATTAACT | GGCGAACTAC | 720 |
| TTACTCTAGC | TTCCCGGCAA | CAATTAATAG | ACTGGATGGA | GGCGGATAAA | GTTGCAGGAC | 780 |
| CACTTCTGCG | CTCGGCCCTT | CCGGCTGGCT | GGTTTATTGC | TGATAAATCT | GGAGCCGGTG | 840 |
| AGCGTGGGTC | TCGCGGTATC | ATTGCAGCAC | TGGGGCCAGA | TGGTAAGCCC | TCCCGTATCG | 900 |
| TAGTTATCTA | CACGACGGGG | AGTCAGGCAA | CTATGGATGA | ACGAAATAGA | CAGATCGCTG | 960 |
| AGATAGGTGC | CTCACTGATT | AAGCATTGGT | AACTGTCAGA | CCAAGTTTAC | TCATATATAC | 1020 |
| TTTAGATTGA | TTTAAAACTT | CATTTTTAAT | TTAAAAGGAT | CTAGGTGAAG | ATCCTTTTTG | 1080 |
| ATAATCTCAT | GACCAAAATC | CCTTAACGTG | AGTTTTCGTT | CCACTGAGCG | TCAGACCCCG | 1140 |
| TAGAAAAGAT | CAAAGGATCT | TCTTGAGATC | CTTTTTTTCT | GCGCGTAATC | TGCTGCTTGC | 1200 |
| AAACAAAAAA | ACCACCGCTA | CCAGCGGTGG | TTTGTTTGCC | GGATCAAGAG | CTACCAACTC | 1260 |
| TTTTTCCGAA | GGTAACTGGC | TTCAGCAGAG | CGCAGATACC | AAATACTGTC | CTTCTAGTGT | 1320 |
| AGCCGTAGTT | AGGCCACCAC | TTCAAGAACT | CTGTAGCACC | GCCTACATAC | CTCGCTCTGC | 1380 |
| TAATCCTGTT | ACCAGTGGCT | GCTGCCAGTG | GCGATAAGTC | GTGTCTTACC | GGGTTGGACT | 1440 |
| CAAGACGATA | GTTACCGGAT | AAGGCGCAGC | GGTCGGGCTG | AACGGGGGGT | TCGTGCACAC | 1500 |
| AGCCCAGCTT | GGAGCGAACG | ACCTACACCG | AACTGAGATA | CCTACAGCGT | GAGCATTGAG | 1560 |
| AAAGCGCCAC | GCTTCCCGAA | GGGAGAAAGG | CGGACAGGTA | TCCGGTAAGC | GGCAGGGTCG | 1620 |
| GAACAGGAGA | GCGCACGAGG | GAGCTTCCAG | GGGGAAACGC | CTGGTATCTT | TATAGTCCTG | 1680 |
| TCGGGTTTCG | CCACCTCTGA | CTTGAGCGTC | GATTTTTGTG | ATGCTCGTCA | GGGGGGCGGA | 1740 |
| GCCTATGGAA | AAACGCCAGC | AACGCGGCCT | TTTTACGGTT | CCTGGCCTTT | TGCTGGCCTT | 1800 |
| TTGCTCACAT | GTTCTTTCCT | GCGTTATCCC | CTGATTCTGT | GGATAACCGT | ATTACCGCCT | 1860 |
| TTGAGTGAGC | TGATACCGCT | CGCCGCAGCC | GAACGACCGA | GCGCAGCGAG | TCAGTGAGCG | 1920 |
| AGGAAGCGGA | AGAGCGCCCA | ATACGCAAAC | CGCCTCTCCC | CGCGCGTTGG | CCGATTCATT | 1980 |
| AATGCAGCTG | GCACGACAGG | TTTCCCGACT | GGAAAGCGGG | CAGTGAGCGC | AACGCAATTA | 2040 |
| ATGTGAGTTA | GCTCACTCAT | TAGGCACCCC | AGGCTTTACA | CTTTATGCTT | CCGGCTCGTA | 2100 |
| TGTTGTGTGG | AATTGTGAGC | GGATAACAAT | TTCACACAGG | AAACAGCTAT | GACCATGATT | 2160 |
| ACGCCAAGCT | CGGAATTAAC | CCTCACTAAA | GGGAACAAAA | GCTGGGACCA | ATTCTCATGT | 2220 |
| TTGACAGCTT | ATCATCGCAG | ATCCTGAGCT | TGTATGGTGC | ACTCTCAGTA | CAATCTGCTC | 2280 |
| TGATGCCGCA | TAGTTAAGCC | AGTATCTGCT | CCCTGCTTGT | GTGTTGGAGG | TCGCTGAGTA | 2340 |
| GTGCGCGAGC | AAAATTTAAG | CTACAACAAG | GCAAGGCTTG | ACCGACAATT | GCATGAAGAA | 2400 |
| TCTGCTTAGG | GTTAGGCGTT | TTGCGCTGCT | TCGGACATTG | ATTATTGACT | AGTTATTAAT | 2460 |
| AGTAATCAAT | TACGGGGTCA | TTAGTTCATA | GCCCATATAT | GGAGTTCCGC | GTTACATAAC | 2520 |
| TTACGGTAAA | TGGCCCGCCT | GGCTGACCGC | CCAACGACCC | CCGCCCATTG | ACGTCAATAA | 2580 |
| TGACGTATGT | TCCCATAGTA | ACGCCAATAG | GGACTTTCCA | TTGACGTCAA | TGGGTGGACT | 2640 |
| ATTTACGGTA | AACTGCCCAC | TTGGCAGTAC | ATCAAGTGTA | TCATATGCCA | AGTACGCCCC | 2700 |
| CTATTGACGT | CAATGACGGT | AAATGGCCCG | CCTGGCATTA | TGCCCAGTAC | ATGACCTTAT | 2760 |
| GGGACTTTCC | TACTTGGCAG | TACATCTACG | TATTAGTCAT | CGCTATTACC | ATGGTGATGC | 2820 |
| GGTTTTGGCA | GTACATCAAT | GGGCGTGGAT | AGCGGTTTGA | CTCACGGGGA | TTTCCAAGTC | 2880 |
| TCCACCCCAT | TGACGTCAAT | GGGAGTTTGT | TTTGGCACCA | AAATCAACGG | GACTTTCCAA | 2940 |
| AATGTCGTAA | CAACTCCGCC | CCATTGACGC | AAATGGGCGG | TAGGCGTGTA | CGGTGGGAGG | 3000 |

-continued

| | | | | | | |
|---|---|---|---|---|---|---|
| TCTATATAAG | CAGAGCTCTC | TGGCTAACTA | GAGAACCCAC | TGCTTACTGG | CTTATCGAAA | 3060 |
| TTAATACGAC | TCACTATAGG | GAGACCCAAG | CTTGGTACCG | AGCTCGGATC | CACTAGTAAC | 3120 |
| GGCCGACAGT | GTGCTGGAAT | TCCTCAAGGT | CGGTCGTTGA | CATTGCTGGG | AGTCCAAGAG | 3180 |
| TCCTCTTATG | TAAGACCTTG | GGCAGGATCT | GATGGGCGTT | CACGGTGGTC | TCCATGCAAC | 3240 |
| GTGCAGAGGT | GAAGCGAAGT | GCACACGGAC | CGGCAGATGA | GAAGGCACAG | ACGGGAGAC | 3300 |
| CGCGTAAAGA | GAGGTGCGCC | CCGTGGTCGG | CTGGAACGGC | AGACGGAGAA | GGGGACGAGA | 3360 |
| GAGTCCCAAG | CGGCCCCGAG | AGGGGTCGTC | CGCGGGATTC | AGCGCCGACG | GGACGTAAAC | 3420 |
| AAAGGACGTC | CCGCGAAGGA | TCCAGTTGGC | AGTACAGCCT | AGCAGCCATG | GAAACGATGT | 3480 |
| ATATTTCCGC | GAGAGGACGA | CAGAATTGTC | AGTTCCGATG | AGCTTTGCTC | CAGACCGGCT | 3540 |
| GCGAGCAAAA | CAAGCGGCTA | GGAGTTCCGC | AGTATGGATC | GGCAGAGGAG | CCACAAAGGT | 3600 |
| TCCACGCATG | CGCTGATGGC | CTATGGCCAA | GCCCAGCCA | GTGGGGTTG | CGTCAGCAAA | 3660 |
| CACTTGGCAC | AGACCAGGCC | GTTGCCGAGC | AACGGGGTAA | AGGTTCATGT | ACTGTTTACT | 3720 |
| TAGAAAGGCT | AGAACTAGTG | GATCCCCGA | ATTAATTCGG | CCCTTATCAG | GGCCATGCAT | 3780 |
| GTCGCGGCCG | CCTCCGCGGC | CGCCTGATGA | GTCCGTGAGG | ACGAAACATG | CATATCAAGC | 3840 |
| TTATCGATAC | CGTCGACCTC | GAGGGGGGGC | CCGGTACCCA | ATTCGCCCTA | TAGTGAGTCG | 3900 |
| TATTACAATT | CACTGGCCGT | CGTTTTACAA | CGTCGTGACT | GGGAAAACCC | TGGCGTTACC | 3960 |
| CAACTTAATC | GCCTTGCAGC | ACATCCCCCT | TTCGCCAGCT | GGCGTAATAG | CGAAGAGGCC | 4020 |
| CGCACCGATC | GCCCTTCCCA | ACAGTTGCGT | AGCCTGAATG | GCGAATGGGA | CGCGCCCTGT | 4080 |
| AGCGGCGCAT | TAAGCGCGGC | GGGTGTGGTG | GTTACGCGCA | GCGTGACCGC | TACACTTGCC | 4140 |
| AGCGCCCTAG | CGCCCGCTCC | TTTCGCTTTC | TTCCCTTCCT | TTCTCGCCAC | GTTCGCCGGC | 4200 |
| TTTCCCCGTC | AAGCTCTAAA | TCGGGGCTC | CCTTTAGGGT | TCCGATTTAG | TGCTTTACGG | 4260 |
| CACCTCGACC | CCAAAAAACT | TGATTTGGGT | GATGGTTCAC | GTAGTGGGCC | ATCGCCCTGA | 4320 |
| TAGACGGTTT | TTCGCCCTTT | GACGTTGGAG | TCCACGTTCT | TTAATAGTGG | ACTCTTGTTC | 4380 |
| CAAACTGGAA | CAACACTCAA | CCCTATCTCG | GTCTATTCTT | TTGATTTATA | AGGGATTTTG | 4440 |
| CCGATTTCGG | CCTATTGGTT | AAAAAATGAG | CTGATTTAAC | AAAATTTAA | CGCGAATTTT | 4500 |
| AACAAAATAT | TAACGTTTAC | AATTT | | | | 4525 |

ANTISENSE CONSTRUCTS DIRECTED AGAINST VIRAL POST-TRANSCRIPTIONAL REGULATORY SEQUENCES

BACKGROUND OF THE INVENTION

It has been shown that several viruses which replicate via reverse transcription rely on cis-acting regulatory sequences to regulate the transport of unspliced and partially spliced transcripts into the cytoplasm where they are expressed as viral proteins. For example, the retrovirus, HIV-1, relies on a cis-acting Rev-response element (RRE), in addition to a Rev protein, to direct export of certain transcripts from the cell nucleus into the cytoplasm, thereby facilitating their expression (See e.g., Cullen et al. (1991) *Science* 16: 346–350; and Rosen et al. (1990) *AIDS* 4: 499–509).

Hepatitis B virus (HBV) is another virus which undergoes reverse transcription during its replication cycle and relies on cis-acting elements to regulate cytoplasmic accumulation of gene transcripts. In particular, all of the known protein products of HBV are encoded on one strand of the circular genome, and are translated from unspliced transcripts. It has been shown that a region encompassing enhancer II and located downstream of the surface gene coding region within surface gene transcripts, named the post-transcriptional regulatory element (PRE), acts in cis at the RNA level to allow transport of these HBV transcripts from the nucleus to the cytoplasm without any effects on transcriptional initiation or cytoplasmic RNA stability (see e.g., Huang et al. (1995) *Molec. and Cell. Biol.* 15(7): 3864–3869; Huang et al. (1994) *J. Virol.* 68(5): 3193–3199; Huang et al. (1993) *Molec. and Cell. Biol.* 13(12): 7476–7486). The effect of relocation of the PRE sequence to a position downstream of the surface gene transcription termination site is a greater than four-fold reduction in the number of cytoplasmic surface gene transcripts, but not of nuclear gene transcripts Huang et al. (1994), supra.

It has been suggested by Huang et al. (1995), supra. that the function of the PRE during the HBV lifecycle is to allow the export of HBV surface gene transcripts into the cytoplasm without these transcripts being spliced. The authors further suggest that the PRE may represent one example of a class of RNA cis elements that activate expression of naturally intronless genes of higher eucaryotes by allowing the export of their transcripts into the cytoplasm.

SUMMARY OF THE INVENTION

The present invention provides antisense constructs which hybridize to and inhibit the function of viral cis-acting post-transcriptional regulatory elements (PREs) which are present in certain viral gene transcripts. PRE sequences targeted by the constructs of the invention have the function of directing export of unspliced viral transcripts from the nucleus to the cytoplasm where the transcripts are translated to viral proteins. These PRE sequences act in cis at the transcriptional level. as part of the viral gene transcript.

In one embodiment, the invention provides a vector (e.g., a plasmid) encoding one or more antisense transcripts which hybridize under intracellular conditions to all or a portion of a PRE within a viral transcript. In a preferred embodiment, viral PRE is derived from hepatitis B virus (HBV), such as the HBV PRE sequence provided in SEQ ID NO:1. The vector can further comprise a nucleotide sequence encoding a cis-acting hammerhead ribozyme which is transcribed with the antisense transcript and causes the transcript to remain nuclear.

In another embodiment, the invention provides an antisense poly- or oligonucleotide which hybridizes to and inhibits the function of a PRE sequence contained in a viral gene transcript, such an HBV transcript. Preferably, the anti-PRE poly- or oligonucleotide is directed against a portion of the PRE which forms part of the secondary structure of the gene transcript.

Antisense constructs of the invention can be delivered to cells either in vitro or in vivo to inhibit production of viruses having PRE sequences. In a preferred embodiment, the constructs are targeted to specific cells (e.g., hepatocytes) in the form of a molecular complex. The complex is made up of the antisense construct releasably linked to a conjugate of a nucleic acid binding agent (e.g., a polycation) and a ligand which binds to a component on the surface of a cell.

DETAILED DESCRIPTION OF THE INVENTION

The present invention provides antisense constructs directed against viral cis-acting post-transcriptional regulatory elements, or "PREs", which function to direct transport of unspliced transcripts from the nucleus of a cell to the cytoplasm where they are expressed.

I. VIRAL "PRE" SEQUENCES

The term "viral cis-acting post-transcriptional regulatory element" or "PRE", as used herein", refers to a viral sequence which acts in cis at the post-transcriptional level (i.e., within a viral gene transcript) to direct or allow cytoplasmic accumulation of unspliced viral gene transcripts. By targeting the PRE sequence with an antisense molecule (e.g., an RNA or a DNA) which hybridizes under intracellular conditions to all or a portion of a VRE, the function of the PRE can be inhibited so that unspliced viral transcripts are retained in the cell nucleus and are, therefore, not expressed as viral proteins.

PRE sequences are commonly found in viruses which replicate via reverse transcription, particularly viruses whose protein products are translated from unspliced transcripts. These sequences regulate the transport of the unspliced viral transcripts from the cell nucleus to the cytoplasm where they are expressed. Examples of viruses for which PRE sequences have been identified include retroviruses, such as human and feline immunodeficiency virus (HIV and FIV) (see e.g., Cullen et al. (1991) *J. Virol.* 65: 1053; and Cullen et al. (1991) *Cell* 58: 423–426), and hepatitis B virus (see e.g., Huang et al. (1995) *Molec. and Cell. Biol.* 15(7): 3864–3869; Huang et al. (1994) *J. Virol.*

68(5): 3193–3199; Huang et al. (1993) *Molec. and Cell. Biol.* 13(12): 7476–7486).

In one embodiment of the invention, the PRE is derived from hepatitis B virus (HBV). A preferred PRE of HBV is a sequence of approximately 587 nucleotides (SEQ ID NO:1) which encompasses enhancer II and is within the transcribed portion of the surface antigen gene (see FIG. 2). This PRE sequence has been shown to function in cis to increase the steady-state levels of surface gene transcripts by facilitating cytoplasmic accumulation of these transcripts.

II. ANTISENSE CONSTRUCTS DIRECTED AGAINST VIRAL PRE SEQUENCES

In one embodiment, the invention provides a vector, such as an expression plasmid, encoding one or more antisense transcripts which hybridize under intracellular conditions to all or a portion of a viral PRE sequence within a viral transcript. Such vectors can be prepared by cloning all or a portion of the viral PRE sequence, in the antisense direction, into an appropriate expression vector containing the necessary genetic regulatory elements required for transcription of the antisense sequence. The antisense PRE sequence can be contained in the vector as a single copy or as multiple copies.

Appropriate regulatory elements which drive gene transcription are well known in the art and include, for example, promoter and enhancer sequences. Suitable promoters include a broad variety of viral promoters, such as SV40 and CMV promoters. Such regulatory sequences are discussed in Goeddel, *Gene expression Technology: Methods in Enzymology*, p. 185, Academic Press, San Diego, Calif. (1990).

In a preferred embodiment, the vector encodes an antisense RNA which hybridizes to and inhibits the function of a PRE sequence of hepatitis B virus (HBV). The term "hybridizes", as used herein, refers to hybridization under intracellular conditions.

HBV is a DNA virus that replicates via reverse transcription. All of its known protein products are encoded on one strand of the circular genome, and they are translated from unspliced transcripts that originate from at least four promoters. HBV relies on certain PRE sequences to direct export of these unspliced transcripts from the cell nucleus to the cytoplasm. A preferred HBV PRE sequence to be targeted by the antisense RNA of the invention has all or a portion of the sequence of SEQ ID NO:1.

In another embodiment of the invention, the vector (e.g., plasmid) encoding the anti-PRE transcript further encodes a cis-acting hammerhead ribozyme which is transcribed with the antisense transcript and causes the transcript to remain nuclear. Generally, the ribozyme is substituted for the polyadenylation signal at the 3' end of the vector. Appropriate ribozyme sequences and methods for preparing vectors containing such sequences are described by Liu et al. (1994) *PNAS* 91: 4258–4262. Once transcribed along with the anti-PRE transcript, the ribozyme RNA acts in cis to keep the anti-PRE transcript in the nucleus where it will hybridize to and inhibit the function of the viral PRE sequence.

In a preferred embodiment, the vector encoding both one or more anti-PRE transcripts and a cis-acting ribozyme is targeted against a PRE derived from HBV. For example, the HBV PRE can have all or a portion of the nucleotide sequence shown in SEQ ID NO:1 followed downstream by a ribozyme sequence. Preparation of one such vector (SEQ ID NO:2) is described below in the exemplification section. This vector contains the HBV PRE sequence of SEQ ID NO:1 cloned in the antisense direction, downstream of the CMV promote, and upstream of a hammerhead ribozyme cassette sequence.

Another aspect of the present invention provides an antisense poly- or oligonucleotide directed against all or a portion of a viral PRE. The term "poly- or oligonucleotide", as used herein, is intended to include a single-stranded DNA or RNA molecule which hybridizes to at least a portion of a viral PRE sequence under intracellular conditions. The degree of complementarity required for appropriately specific hybridization to a target viral PRE sequence under intracellular conditions can be determined empirically.

Anti-PRE poly- or oligonucleotides of the invention can range in length from about 15 to about 40 bases, more preferably about 20 to about 35 bases, and most preferably about 25 to about 31 bases. Preferred antisense poly- or oligonucleotides hybridize to a portion of a PRE sequence (contained in viral gene transcript) which forms part of the secondary structure of the transcript and, therefore, are likely involved in protein binding.

Figure 2:
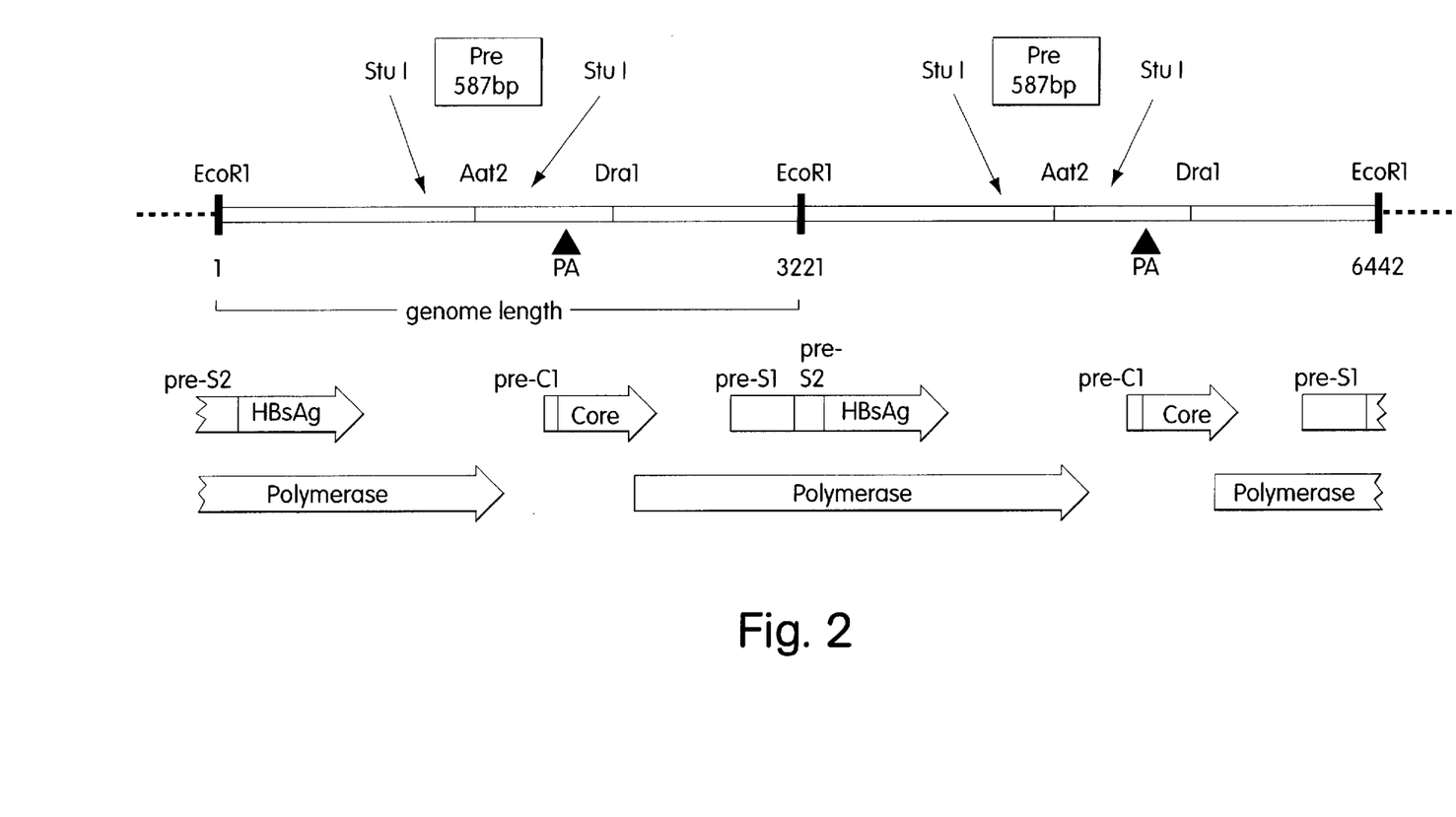
FIG. 2 shows a map of the head-to-tail Dimer (pADW-HTD) of the hepatitis B virus (HBV) genome, including a 587 base pair stu-1 restriction fragment containing the HBV post-transcriptional regulatory (PRE) sequence.

In one embodiment, the anti-PRE poly- or oligonucleotide hybridizes to all or a portion of a PRE contained in an HBV transcript, such as the HBV PRE shown in FIG. 2 (SEQ ID NO:1). Preferably, the portion of the HBV PRE sequence targeted by the anti-PRE poly- or oligonucleotides of the invention is involved in forming the secondary structure of the HBV transcript.

Anti-PRE poly-or oligonucleotides of the invention can be chemically synthesized using standard techniques well known in the art. For example, various methods of chemically synthesizing polydeoxynucleotides are known, including solid-phase synthesis which, like peptide synthesis, has been fully automated in commercially available DNA synthesizers (See e.g., Itakura et al., U.S. Pat. No. 4,598,049; Caruthers et al., U.S. Pat. No. 4,458,066; and Itakura, U.S. Pat. Nos. 4,401,796 and 4,373,071, incorporated by reference herein).

However, when administered in vivo, synthetic and natural oligonucleotides are subject to degradation by exo- and endonucleases in a manner equivalent to any cellular nucleic acid. Accordingly, preferred anti-PRE poly- or oligonucleotides of the invention are chemically modified to provide substantial nuclease resistance. Such chemically modified poly- or oligonucleotides include, for example, phosphorothioate oligonucleotides, in which one of the phosphate oxygens is replaced by a sulfer atom (See e.g., U.S. Pat. No. 5,262,530, the teachings of which are incorporated by reference herein). Phosphorothioates may be synthesized using automated techniques employing either phosphoramidite or phosphonate chemistries. Other modified poly- or oligonucleotides with increased stability include, for example, nonionic DNA analogs, such as alkyl- or arylphosphonates, in which the charged phosphate oxygen is replaced by an alkyl or aryl group (see e.g., U.S. Pat. No. 4,469,863, the teachings of which are incorporated by reference herein), and alkylphosphotriesters, in which the charged oxygen moiety is alkylated (See e.g., U.S. Pat. No. 5,023,243 and European Patent No: 092,574, the teachings of which are incorporated by reference herein). Both of these DNA analogs can be prepared by automated solid-phase synthesis using commercially available reagents. It is also known that addition of a diol, such as tetraethyleneglycol or hexaethyleneglycol, at either or both termini of a synthetic oligonucleotide confers substantial nuclease resistance. (See e.g., U.S. Pat. No. 5,245,022, the teachings of which are incorporated by reference herein).

III. DELIVERY OF ANTI-PRE CONSTRUCTS TO CELLS

Antisense constructs of the invention can be delivered to cells either in vitro or in vivo to inhibit production of HBV.

For example, the constructs can be transfected into cells in vitro using standard transfection techniques, such as calcium phosphate precipitation. Alternatively, the plasmid can be delivered to cells in vivo by, for example, intravenous or intramuscular injection.

In a preferred embodiment of the invention, the constructs are targeted for delivery to a specific cell by releasably linking the plasmid to a carrier molecule made up of a nucleic acid binding agent and a ligand which binds to a component on the surface of a cell, thereby forming a polynucleotide-carrier complex.

The carrier molecule of the polynucleotide-carrier complex performs at least two functions: (1) it binds the polynucleotide (e.g., the plasmid) in a manner which is sufficiently stable (either in vivo, ex vivo, or in vitro) to prevent significant uncoupling of the polynucleotide extracellularly prior to internalization by a target cell, and (2) it binds to a component on the surface of a target cell so that the polynucleotide-carrier complex is internalized by the cell. Generally, the carrier is made up of a cell-specific ligand and a cationic moiety which, for example are conjugated. The cell-specific ligand binds to a cell surface component, such as a protein, polypeptide, carbohydrate, lipid or combination thereof. It typically binds to a cell surface receptor. The cationic moiety binds, e.g., electrostatically, to the polynucleotide.

The ligand of the carrier molecule can be any natural or synthetic ligand which binds a cell surface receptor. The ligand can be a protein, polypeptide, glycoprotein, glycopeptide or glycolipid which has functional groups that are exposed sufficiently to be recognized by the cell surface component. It can also be a component of a biological organism such as a virus, cells (e.g., mammalian, bacterial, protozoan).

Alternatively, the ligand can comprise an antibody, antibody fragment (e.g., an F(ab')$_2$ fragment) or analogues thereof (e.g., single chain antibodies) which binds the cell surface component (see e.g., Chen et al. (1994) *FEBS Letters* 338:167–169, Ferkol et al. (1993) *J Clin. Invest.* 92:2394–2400, and Rojanasakul et al. (1994) *Pharmaceutical Res.* 11(12):1731–1736). Such antibodies can be produced by standard procedures.

Ligands useful in forming the carrier will vary according to the particular cell to be targeted. For targeting hepatocytes, proteins and polypeptides containing galactose-terminal carbohydrates, such as carbohydrate trees obtained from natural glycoproteins, can be used. For example, natural glycoproteins that either contain terminal galactose residues or can be enzymatically treated to expose terminal galactose residues (e.g., by chemical or enzymatic desialylation) can be used. In one embodiment, the ligand is an asialoglycoprotein, such as asialoorosomucoid, asialofetuin or desialylated vesicular stomatitis virus.

Alternatively, suitable ligands for targeting hepatocytes can be prepared by chemically coupling galactose-terminal carbohydrates (e.g., galactose, mannose, lactose, arabinogalactan etc.) to nongalactose-bearing proteins or polypeptides (e.g., polycations) by, for example, reductive lactosamination. Methods of forming a broad variety of other synthetic glycoproteins having exposed terminal galactose residues, all of which can be used to target hepatocytes, are described, for example, by Chen et al. (1994) *Human Gene Therapy* 5:429–435 and Ferkol et al. (1993) *FASEB* 7: 1081–1091 (galactosylation of polycationic histones and albumins using EDC); Perales et al. (1994) *PNAS* 91:4086–4090 and Midoux et al. (1993) *Nucleic Acids Research* 21(4):871–878 (lactosylation and galactosylation of polylysine using α-D-galactopyranosyl phenylisothiocyanate and 4-isothiocyanatophenyl β-D-lactoside); Martinez-Fong (1994) *Hepatology* 20(6):1602–1608 (lactosylation of polylysine using sodium cyanoborohydride and preparation of asialofetuin-polylysine conjugates using SPDP); and Plank et al. (1992) *Bioconjugate Chem.* 3:533–539 (reductive coupling of four terminal galactose residues to a synthetic carrier peptide, followed by linking the carrier to polylysine using SPDP).

For targeting the polynucleotide-carrier complex to other cell surface receptors, the carrier component of the complex can comprise other types of ligands. For example, mannose can be used to target macrophages (lymphoma) and Kupffer cells, mannose 6-phosphate glycoproteins can be used to target fibroblasts (fibro-sarcoma), intrinsic factor-vitamin B12 and bile acids (See Kramer et al. (1992) *J. Biol. Chem.* 267:18598–18604) can be used to target enterocytes, insulin can be used to target fat cells and muscle cells (see e.g., Rosenkranz et al. (1992) *Experimental Cell Research* 199:323–329 and Huckett et al. (1990) *Chemical Pharmacology* 40(2):253–263), transferrin can be used to target smooth muscle cells (see e.g., Wagner et al. (1990) *PNAS* 87:3410–3414 and U.S. Pat. No. 5,354,844 (Beug et al.)), Apolipoprotein E can be used to target nerve cells, and pulmonary surfactants, such as Protein A, can be used to target epithelial cells (see e.g., Ross et al. (1995) *Human Gene Therapy* 6:31–40).

The cationic moiety of the carrier molecule can be any positively charged species capable of electrostatically binding to negatively charged polynucleotides. Preferred cationic moieties for use in the carrier are polycations, such as polylysine (e.g., poly-L-lysine), polyarginine, polyornithine, spermine, basic proteins such as histones (Chen et al., supra.), avidin, protamines (see e.g., Wagner et al., supra.), modified albumin (i.e., N-acylurea albumin) (see e.g., Huckett et al., supra.) and polyamidoamine cascade polymers (see e.g., Haensler et al. (1993) *Bioconjugate Chem.* 4: 372–379). A preferred polycation is polylysine (e.g., ranging from 3,800 to 60,000 daltons).

In one embodiment, the carrier comprises polylysine having a molecular weight of about 17,000 daltons (purchased as the hydrogen bromide salt having a MW of a 26,000 daltons), corresponding to a chain length of approximately 100–120 lysine residues. In another embodiment, the carrier comprises a polycation having a molecular weight of about 2,600 daltons (purchased as the hydrogen bromide salt having a MW of a 4,000 daltons), corresponding to a chain length of approximately 15–10 lysine residues.

The carrier can be formed by linking a cationic moiety and a cell-specific ligand using standard cross-linking reagents which are well known in the art. The linkage is typically covalent. A preferred linkage is a peptide bond. This can be formed with a water soluble carbodiimide, such as 1-ethyl-3-(3-dimethylaminopropyl)carbodiimide hydrochloride (EDC), as described by McKee et al (1994) *Bioconjugate Chem.* 5: 306–311 or Jung, G. et al. (1981) *Biochem. Biophys. Res. Commun.* 101: 599–606 or Grabarek et al. (1990) *Anal. Biochem.* 185:131. Alternative linkages are disulfide bonds which can be formed using cross-linking reagents, such as N-Succinimidyl 3-(2-pyridyldithio) propionate (SPDP), N-hydroxysuccinimidyl ester of chlorambucil, N-Succinimidyl-(4-Iodoacetyl) aminobenzoate) (SIAB), Sulfo-SIAB, and Sulfo-succinimidyl-4-maleimidophenyl-butyrate (Sulfo-SMPB). Strong noncovalent linkages, such as avidin-biotin interactions, can also be used to link cationic moieties to a variety of cell binding agents to form suitable carrier molecules.

The linkage reaction can be optimized for the particular cationic moiety and cell binding agent used to form the carrier. The optimal ratio (w:w) of cationic moiety to cell binding agent can be determined empirically. This ratio will vary with the size of the cationic moiety (e.g., polycation) being used in the carrier, and with the size of the polynucleotide to be complexed. However, this ratio generally ranges from about 0.2–5.0 (cationic moiety: ligand). Uncoupled components and aggregates can be separated from the carrier by molecular sieve or ion exchange chromatography (e.g., Aquapore™ cation exchange, Rainin).

In one embodiment of the invention, a carrier made up of a conjugate of asialoorosomucoid and polylysine is formed with the cross linking agent 1-(3-dimethylaminopropyl)-3-ethyl carbodiimide. After dialysis, the conjugate is separated from unconjugated components by preparative acid-urea polyacrylamide gel electrophoresis (pH 4–5). The conjugate can be further purified on the carboxymethyl functionalized column (see U.S. patent application Ser. No. 08/043,008, filed Apr. 5, 1993, the teachings of which are incorporated by reference herein).

Following formation of the carrier molecule, the polynucleotide (e.g., anti-PRE vector or oligonucleotide) is linked to the carrier so that (a) the polynucleotide is sufficiently stable (either in vivo, ex vivo, or in vitro) to prevent significant uncoupling of the polynucleotide extracellularly prior to internalization by the target cell, (b) the polynucleotide is released in functional form under appropriate conditions within the cell, (c) the polynucleotide is not damaged and (d) the carrier retains its capacity to bind to cells. Generally, the linkage between the carrier and the polynucleotide is noncovalent. Appropriate noncovalent bonds include, for example, electrostatic bonds, hydrogen bonds, hydrophobic bonds, anti-polynucleotide antibody binding, linkages mediated by intercalating agents, and streptavidin or avidin binding to polynucleotide-containing biotinylated nucleotides. However, the carrier can also be directly (e.g., covalently) linked to the polynucleotide using, for example, chemical cross-linking agents (e.g., as described in WO-A-91/04753 (Cetus Corp.), entitled "Conjugates of Antisense Oligonucleotides and Therapeutic Uses Thereof").

To form polynucleotide-carrier complexes, a solution containing carrier molecules is combined with the anti-PRE polynucleotide to be complexed. The solution contains a sufficient amount of a charge shielding agent to inhibit aggregation of the carrier molecules (i.e., aggregation which would occur in the absence of a charge shielding agent). In one embodiment, the carrier solution is prepared by forming carrier molecules, as described above (e.g., by conjugation of a cationic moiety and a cell binding agent), and then mixing the carrier molecules with a sufficient amount of a charge shielding agent to inhibit aggregation of the carrier molecules.

The term "charge shielding agent", as used herein, is intended to include any agent which is capable of (a) reducing charge interactions (e.g., hydrogen bonding) between individual cationic carrier molecules and/or between different parts of the same carrier molecule; and/or (b) reducing charge interactions between cationic carrier molecules and the solvent.

The term "inhibit aggregation," as used herein, refers to disaggregation and/or to prevention of aggregation of cationic carrier molecules.

The term "sufficient to inhibit aggregation of the carrier molecules," as used herein, refers to a level of disaggregation at which the carrier molecules, when complexed to polynucleotide, are easily taken up by cells and/or can easily pass through physiological barriers (e.g., blood/tissue barriers). Generally, this level of dispersity is achieved when the carrier molecules have a radius of about 20 nm or less, preferably about 15 nm or less and most preferably about 10 nm or less, as measured by laser light scattering analysis. Other methods of determining the level of aggregation of carrier molecules (alone or complexed to polynucleotide) include, for example, sucrose density gradient analysis, electron microscopy (EM), circular dichroism (CD), and spectrophotometry (e.g., absorbance at 260 nm).

In a preferred embodiment of the invention, the charge shielding agent is a salt. Suitable salts include, for example, sodium chloride (NaCl), sodium sulfate ($Na_2SO_4$), sodium phosphate ($NaH_2PO_4$), ammonium sulfate (($NH_4$)$SO_4$), ammonium phosphate ($NH_4H_2PO_4$), potassium sulfate ($K_2SO_4$), potassium phosphate ($KH_2PO_4$), potassium chloride (KCl), magnesium sulfate ($MgSO_4$), magnesium phosphate ($MgHPO_4$), magnesium chloride ($MgCl_2$), and lithium chloride (LiCl) and a variety of others. In a particularly preferred embodiment, the salt is sodium chloride (NaCl).

Other charge shielding agents which can be used to substantially disaggregate the carrier molecules include, for example, detergents and amphiphile surfactants such as the BRIJ family of polyoxyethylene fatty ethers, the SPAN sorbitan fatty acid esters, and the TWEEN polyoxyethylene derivatives of sorbitan fatty acid esters, all available from ICI Americas, Inc. of Wilmington, Del.

When using a salt (e.g., NaCl) as the charge shielding agent, the appropriate amount of salt to inhibit aggregation of the carrier molecules will vary according to the concentration of the carrier molecules. However, this concentration is generally at least about 1.0M or more. For example, for solutions containing carrier molecules at a concentration of about 0.5–20 mg/mL, the salt can be added to a concentration of about 1.0–10M. In a preferred embodiment, the carrier molecules are present in the carrier solution at a concentration of about 3.0–7.0 mg/mL, preferably about 5.0–6.0 mg/mL, and most preferably about 5.6 mg/mL. At these concentrations of carrier molecules, the carrier solutions can be prepared with salt concentrations of about 1.0–5.0M, preferably about 4.0–5.0M, and most preferably about 4.7M, respectively.

However, the appropriate amount of any given charge shielding agent to inhibit aggregation of carrier molecules can be determined empirically. For example, samples of carrier molecules can be prepared at various concentrations of a charge shielding agent as previously described, and the level of aggregation of the carrier molecules can then be examined by any of the techniques disclosed above (e.g., laser light scattering analysis, sucrose density gradient analysis, electron microscopy (EM), circular dichroism (CD), and spectrophotometry).

In addition to a charge shielding agent, the carrier solution can also optionally contain other dispersing agents to further inhibit aggregation of the carrier molecules. Aggregation of cationic carrier molecules is believed to result largely from intermolecular and intramolecular associations (e.g., hydrogen bonding) involving the net positive charge of the carrier molecules. Agents which reduce the net positive charge of the carrier molecules, therefore, can diminish these molecular associations and promote dispersity of the cationic carrier molecules.

Accordingly, in one embodiment of the invention, the carrier solution comprises a charge neutralizing agent, in addition to the charge shielding agent. The term "charge neutralizing agent", as used herein, is intended to include any agent capable of neutralizing a portion of the positive charge of cationic carrier molecules (i.e., by deprotonation). In a preferred embodiment of the invention, the charge neutralizing agent is a base. Suitable bases include, for example, sodium hydroxide (NaOH), potassium hydroxide (KOH), ammonium hydroxide (NH$_4$OH), alkylamines, alkoxides and triethanolamines. In a particularly preferred embodiment, the base is sodium hydroxide.

The cationic carrier solution contains the charge neutralizing agent in an amount sufficient to neutralize a portion of the positive charge of the carrier molecules. This partial neutralization reduces charge associations and aggregation of the carrier molecules, while still maintaining an overall net positive charge associated with the carrier molecules (so that they are able to electrostatically bind negatively charged polynucleotides). In one embodiment of the invention, the charge neutralizing agent is added to the carrier solution in an amount sufficient to neutralize about 5 to 20% (e.g., about 10%) of the positive charge of the carrier molecules. The charge neutralizing agent may be added to the carrier solution before, after or concurrently with the charge shielding agent.

When using a base as the charge neutralizing agent, the carrier solution can be prepared with a concentration of base (e.g., NaOH) of about 10–1000 mM, preferably about 10–100 mM, more preferably about 50–70 mM, and most preferably about 59 mM, for carrier solutions containing carrier molecules at a concentration of about 0.5–20 mg/mL, preferably about 3–7 mg/mL, more preferably about 5–6 mg/mL, and most preferably about 5.6 mg/mL, respectively. The carrier solution can then be mixed vigorously to promote disaggregation of molecular carrier aggregates.

The polynucleotide to be complexed is combined (and allowed to equilibrate) with the carrier solution to form substantially disperse and soluble polynucleotide-carrier complexes. The polynucleotide is combined with the carrier solution so that the polynucleotide-carrier solution contains a final concentration of charge shielding agent and, optionally, charge neutralizing agent which does not damage or induce any substantial conformational change (e.g., denature) in the polynucleotide so that it remains substantially functional and in a form suitable for complexing with the carrier molecules. Generally, this corresponds to a final concentration of charge shielding agent (e.g., salt) of less than 1.0M, preferably less than 0.75M, and most preferably less than 0.5M (e.g., about 0.15–0.5M), and a concentration of charge neutralizing agent of less than 10 mM, preferably less than 4.0 mM, and most preferably about 2.0 mM.

In one embodiment, the polynucleotide is diluted, for example, with nanopure water, prior to (or concurrently with) being combined with a carrier solution to a concentration which, when combined with the carrier solution, results in the desired final concentration of charge shielding agent (e.g., salt) and charge neutralizing agent (e.g., base). When adding the polynucleotide to a carrier solution containing a salt (e.g., NaCl) as the charge shielding agent, the polynucleotide can be diluted to a concentration which results in a final salt concentration (i.e., after mixing with carrier solution) of less than 1.0M, preferably less than 0.5M, more preferably about 0.15–0.5M and most preferably about 0.3M (about two times physiological). At this concentration of salt, the carrier molecules maintain a high level of dispersity and the polynucleotide remains functional.

If the carrier solution contains a charge neutralizing agent (e.g., a base), along with the charge shielding agent, then the final concentration of charge neutralizing agent in the carrier solution, following addition of the polynucleotide, should also be a concentration which does not substantially damage, alter, or inhibit the function of the polynucleotide. For example, when using a base as the charge neutralizing agent, the polynucleotide-carrier solution can contain a final base concentration of less than 50 mM, preferably less than 10 mM, more preferably less than 4.0 mM (e.g., about 1.0–4.0 mM), and most preferably about 2.0 mM.

In a preferred embodiment of the invention, the final solution in which the polynucleotide-carrier complexes are formed has (a) a carrier molecule concentration of about 3.0–7.0 mg/mL, preferably about 5.0–6.0 mg/mL, (b) a salt concentration of about 0.15–0.5M, preferably about 0.3M, (c) a base concentration of about 1.0–4.0 mM, preferably about 2.0 mM and (c) an appropriate final concentration of DNA (e.g., 10 µg/mL).

The polynucleotide is combined with the carrier solution in an amount appropriate to form stable complexes which remain soluble in solution. Generally, the polynucleotide is added to the carrier solution in a weight to weight (w:w) ratio (polynucleotide to carrier) of about 1:0.2–1:20, (e.g., about 1:1–1:10, or about 1:1.5–1:5). Complexes formed with these weight ratios (polynucleotide to carrier) have corresponding charge neutralization ratios (i.e., percent neutralization of negatively charge polynucleotide by positively charged carrier) of about 10–1000% (e.g., about 50–500%, or about 75–250%), respectively.

The performance of a given polynucleotide-carrier complex can be affected by the level of polynucleotide charge neutralization in the complex. The optimal level of polynucleotide charge neutralization for a given complex can depend on a variety of factors, including the nature of the polynucleotide (e.g., plasmid DNA) and the size and charge of the particular cationic carrier molecule used. While appropriate levels of polynucleotide charge neutralization for complexes generally fall within the ranges provided above, the optimal level for a given complex can be determined empirically. For example, a series of preparations can be made for a particular complex each with varying degrees of polynucleotide charge neutralization. The performance of these samples can then be tested by, for example, measuring levels of expression obtained with each sample either in vitro or in in vivo expression assays.

Additional steps also can be taken which further diminish aggregation of complexes, as well as reduce the size of the complexes and increase their homogeneity, thereby improving their performance (e.g., level of gene expression). Such measures include, for example, extrusion of the complexes, temperature variations, pH changes and measures which diminish inhibitory actions which occur in vivo (e.g., opsonization of the complex by inhibitory factors present in blood serum).

Accordingly, in another embodiment of the invention, the polynucleotide-carrier complexes are extruded through an appropriate filter after being formed but prior to being administered to cells (either in vitro or in vivo). The term "extrusion" or "extruded", as used herein, means passage of the complexes through a filtering apparatus, followed by collection of the filtered product. Extrusion of complexes significantly (1) decreases the size of the complexes (2) increases the homogeneity of the complexes, and (3) improves the performance of the complexes, as measured by gene expression levels. While any extrusion apparatus which diminishes larger complexes and increases the proportion of smaller, more homogenous complexes may be used, a preferred apparatus for extruding complexes is a 50 nm filter attached to an Emulsi-Flex-C5 (Avestin, Inc. Ottawa, Canada).

Compositions of polynucleotide-carrier complexes, formed as described herein, can be used either in vitro or in vivo to target the anti-PRE constructs of the invention to selected cells. For in vitro delivery of anti-PRE constructs of the invention, cultured cells can be incubated with the polynucleotide-carrier complexes in an appropriate medium under conditions conducive to endocytotic uptake by the cells.

For in vivo delivery of anti-PRE constructs of the invention to cells, the polynucleotide-carrier complexes can be administered to a subject in a pharmaceutically acceptable vehicle. The term "pharmaceutically acceptable carrier", as used herein, is intended to include any physiologically acceptable carrier for stabilizing polynucleotide-carrier complexes of the present invention for administration in vivo, including, for example, saline and aqueous buffer solutions, solvents, dispersion media, antibacterial and antifingal agents, isotonic and absorption delaying agents, and the like. The use of such media and agents for pharmaceutically active substances is well known in the art. Except insofar as any conventional media is incompatible with the polynucleotide-carrier complexes of the present invention, use thereof in a therapeutic composition is contemplated.

In all cases, the pharmaceutical composition must be sterile and must be fluid to the extent that easy syringability exists. It must be stable under the conditions of manufacture and storage and must be preserved against the contaminating action or microorganisms such as bacteria and fungi. Protection of the polynucleotide-carrier complexes from degradative enzymes (e.g., nucleases) can be achieved by including in the composition a protective coating or nuclease inhibitor. Prevention of the action of microorganisms can be achieved by various anti-bacterial and anti-fungal agents, for example, parabens, chlorobutanol, phenol, ascorbic acid, thimerosal, and the like.

Polynucleotide-carrier complexes of the invention may be administered in vivo by any suitable route of administration. The appropriate dosage may vary according to the selected route of administration. The complexes are preferably injected intravenously in solution containing a pharmaceutically acceptable carrier, as defined herein. Sterile injectable solutions can be prepared by incorporating the polynucleotide-carrier complexes in the required amount in an appropriate buffer with one or a combination of ingredients enumerated above, as required, followed by filtered sterilization. Other suitable routes of administration include intravascular, subcutaneous (including slow-release implants), topical and oral.

Appropriate dosages may be determined empirically, as is routinely practiced in the art. Mice can be administered dosages of up to 1.0 mg of polynucleotide per 20 g of mouse, or about 1.0 mL of complex per 1.4 mL of mouse blood.

This invention is illustrated further by the following examples which should not be construed as further limiting the subject invention. The contents of all references and published patent applications cited throughout this application are hereby incorporated by reference.

EXAMPLE 1

Preparation of an Expression Vector Encoding a Nuclear-Retained Antisense Transcript Directed Against a Hepatitis B Virus PRE Sequence In this example, an expression vector which produces a nuclear-retained antisense RNA directed against a 587 base pair sequence of HBV (Adw) was prepared. The 587 base pair antisense sequence covers partial sequences to HBV enhancers I and II, as well as a post-transcriptional regulatory element (PRE) which is hypothesized to allow export of HBV transcripts which do not interact with the normal cellular splicing pathway of the cell (see FIG. 2; see also e.g., Huang et al. (1995) Molec. and Cell. Biol. 15(7): 3864–3869). The antisense sequence was followed by a cis-acting hammerhead ribozyme which results in the antisense transcript remaining nuclear (Liu et al. (1994) PNAS 91: 4258–4262).

To prepare the expression vector, the 587 base pair PRE element (complementary to bases 1118 to 1704 (SEQ ID NO:1) of the hepatitis B virus (HBV) genome), was excised as an stu-1 restriction fragment from plasmid pADW-HTD HBV (see FIG. 2), containing two head-to-tail copies of the HBV genome. The fragment, which contained the PRE sequence (SEQ ID NO:1), was then cloned into an expression vector, pCMV-RZ (kindly provided as pRSV-RZ by Dr. Gordon Carmichael at The University of Connecticut, Farmington, Conn., and modified to contain the CMV promoter by Dr. Charles R. Ill at The Immune Response Corporation, Carlsbad, Calif.) in the antisense orientation, as either one or two copies. The PRE fragment was inserted into the vector at a position downstream from the CMV promoter and 5' of a histone stem loop structure, followed by a hammerhead ribozyme sequence. The full-length nucleotide sequence of the one copy antisense plasmid, pCMVasPRE-RZ, is provided in SEQ ID NO:2.

EXAMPLE 2

Inhibition of HBV Production Using Antisense Plasmids Directed Against a PRE

To study the HBV antiviral effect of the expression plasmids constructed in Example 1, each plasmid was co-transfected with a plasmid coding for two copies of the HBV genome (pADW-HTD) into HUH-711 (human carcinoma) cells via calcium phosphate precipitation (O'Mahoney et al. (1994) DNA & Cell Biol. 13(12): 1227–1232), followed by measurement of HBV surface antigen (HBSAg) production. Plasmids producing nuclear-retained antisense transcripts directed against either the luciferase gene or the human growth hormone gene, were used as controls.

Cells were co-transfected with a ratio of pADW-HTD to antisense plasmid of 1:5 (6 $\mu$g pADW-HTD to 36 $\mu$g antisense plasmid). At the time of mixing the calcium phosphate/plasmid mixtures with cell cultures, the cells were approximately 85% confluent in T-75 flasks, in log growth, at 15 mL DMEM.

Sixteen hours after the initial addition of calcium phosphate/plasmid mixtures to cells, low density cell cultures were washed and 15 mL of fresh DMEM medium was added to flasks. For high density cell cultures, cells were washed, trypsinized, and plated into 12-well plates (2 plates per transfection).

Supernatants were collected from 3 wells of each transfection at 24, 28, 32, 48, 52, and 56 hours after plating into plates. At each collection time, the medium in each of the remaining wells was changed. Samples were then assayed for HBSAg using the Abbott Diagnostics' AUSZYME™ Monoclonal Diagnostic Kit. A standard curve was generated from purified HBSAg (20 mg/mL).

Figure 1:
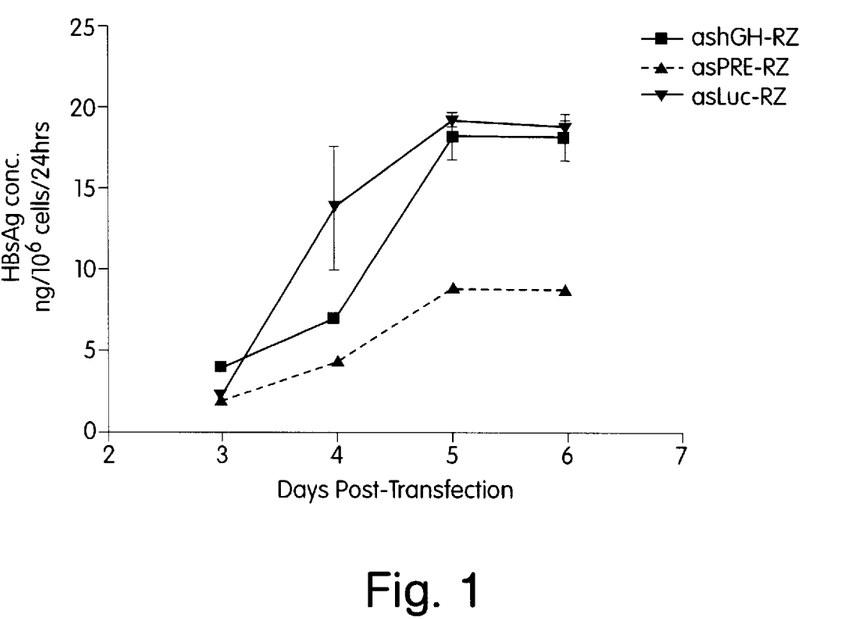
FIG. 1 is a graphic representation of the levels of HBV surface antigen expressed in HUH-711 cells co-transfected with a hepatitis B virus PRE antisense expression plasmid (asPRE-RZ) and a plasmid containing two copies of the HBV genome (HBVpADW-HTD). Plasmid asPRE-RZ contained one copy of the HBV post-transcriptional regulatory (PRE) sequence (SEQ ID NO:1) cloned in the antisense direction upstream from a hammerhead ribozyme. Plasmid asLuc (control) contained a copy of the luciferase gene cloned in the antisense direction upstream from a hammerhead ribozyme. Plasmid asHGH-RZ (control) contained a copy of the human growth hormone gene cloned in the antisense direction upstream from a hammerhead ribozyme.

As shown in FIG. 1, the plasmid containing the PRE sequence (one copy) cloned in the antisense direction (asPRE-RZ) significantly reduced HBV transcripts compared to the control plasmids, ashGH-RZ and asLuc-RZ, as determined by production of HBSAg.

Overall, these examples demonstrate that HBV production can be inhibited by targeting the PRE sequence with a nuclear-retained antisense transcript.

EQUIVALENTS

Although the invention has been described with reference to its preferred embodiments, other embodiments can achieve the same results. Those skilled in the art will recognize or be able to ascertain using no more than routine experimentation, numerous equivalents to the specific embodiments described herein. Such equivalents are considered to be within the scope of this invention and are encompassed by the following claims.

What is claimed is:

1. A vector encoding one or more antisense transcripts which are complementary to all or a portion of a hepatitis B viral cis-acting post-transcriptional regulatory element, said post-transcriptional regulatory element comprising the nucleotide sequence shown in SEQ ID NO:1 and having the function of directing export of the viral transcript from the nucleus to the cytoplasm of a cell.

2. The vector of claim 1 further comprising a nucleotide sequence encoding a cis-acting hammerhead ribozyme which is transcribed with the antisense transcript and causes the transcript to remain nuclear.

3. The vector of claim 1 comprising the nucleotide sequence of SEQ ID NO:2.

4. A molecular complex comprising the vector of claim 1 releasably linked to a conjugate of a nucleic acid binding agent and a ligand which binds to a component on the surface of a cell.

5. The molecular complex of claim 4 wherein the nucleic acid binding agent is a polycation.

6. The molecular complex of claim 5 wherein the polycation is polylysine.

7. The molecular complex of claim 4 wherein the ligand contains a terminal carbohydrate residue.

8. The molecular complex of claim 7 wherein the ligand binds to the asialoglycoprotein receptor.

9. The molecular complex of claim 8 wherein the ligand is an asialoglycoprotein.

10. The molecular complex of claim 4 wherein the vector further comprises a nucleotide sequence encoding a cis-acting hammerhead ribozyme which is transcribed with the antisense transcript and causes the transcript to remain nuclear.

11. The molecular complex of claim 8 wherein the vector comprises the nucleotide sequence shown in SEQ ID NO:2.

* * * * *